(12) United States Patent
O'Connell, Jr.

(10) Patent No.: US 9,808,568 B2
(45) Date of Patent: Nov. 7, 2017

(54) APPARATUS AND METHOD FOR SEPARATING AND CONCENTRATING A COMPONENT OF A FLUID

(71) Applicant: Biomet Biologics, LLC, Warsaw, IN (US)

(72) Inventor: Patrick S. O'Connell, Jr., Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 282 days.

(21) Appl. No.: 14/803,440

(22) Filed: Jul. 20, 2015

(65) Prior Publication Data

US 2016/0015884 A1  Jan. 21, 2016

Related U.S. Application Data

(63) Continuation of application No. 13/434,245, filed on Mar. 29, 2012, now Pat. No. 9,120,095.

(51) Int. Cl.
| | | |
|---|---|---|
| A61M 1/36 | (2006.01) | |
| B01D 15/26 | (2006.01) | |
| B01D 21/26 | (2006.01) | |
| G01N 33/49 | (2006.01) | |
| A61M 39/08 | (2006.01) | |
| A61M 39/24 | (2006.01) | |
| B01L 3/00 | (2006.01) | |

(52) U.S. Cl.
CPC ........ *A61M 1/3693* (2013.01); *A61M 1/3687* (2013.01); *A61M 39/08* (2013.01); *A61M 39/24* (2013.01); *B01D 15/26* (2013.01); *B01D 21/262* (2013.01); *B01L 3/502* (2013.01); *B01L 3/5021* (2013.01); *B01L 3/50215* (2013.01); *G01N 33/491* (2013.01); *B01L 2200/026* (2013.01); *B01L 2300/046* (2013.01); *B01L 2300/047* (2013.01); *B01L 2300/0681* (2013.01); *B01L 2400/0605* (2013.01)

(58) Field of Classification Search
CPC .. A61M 1/3687; A61M 1/3693; A61M 39/08; A61M 39/24; B01D 15/26; B01D 21/262; B01L 2200/026; B01L 2300/046; B01L 2300/047; B01L 2300/0681; B01L 2400/0605; B01L 3/502; B01L 3/5021; B01L 3/50215; G01N 33/491
See application file for complete search history.

(56) References Cited

U.S. PATENT DOCUMENTS 5,840,502 A * 11/1998 Van Vlasselaer ..... B01L 3/5021
  210/781
2005/0184012 A1 * 8/2005 Coull ................... A61M 1/029
  210/787

* cited by examiner

*Primary Examiner* — John Kim
(74) *Attorney, Agent, or Firm* — Schwegman Lundberg & Woessner, P.A.

(57) ABSTRACT

A system for separating and concentrating a component of a whole material is disclosed. The whole material can include a material that has more than one component, such as whole blood that can include at least red blood cells, monocytes, and plasma. The system can include a substantially single container including a separation section and a concentration section wherein a component can be moved from the separation section, after a separation, to the concentration section to be concentrated. The concentrated component can then be withdrawn from the separation and concentration container for a selected procedure.

15 Claims, 9 Drawing Sheets

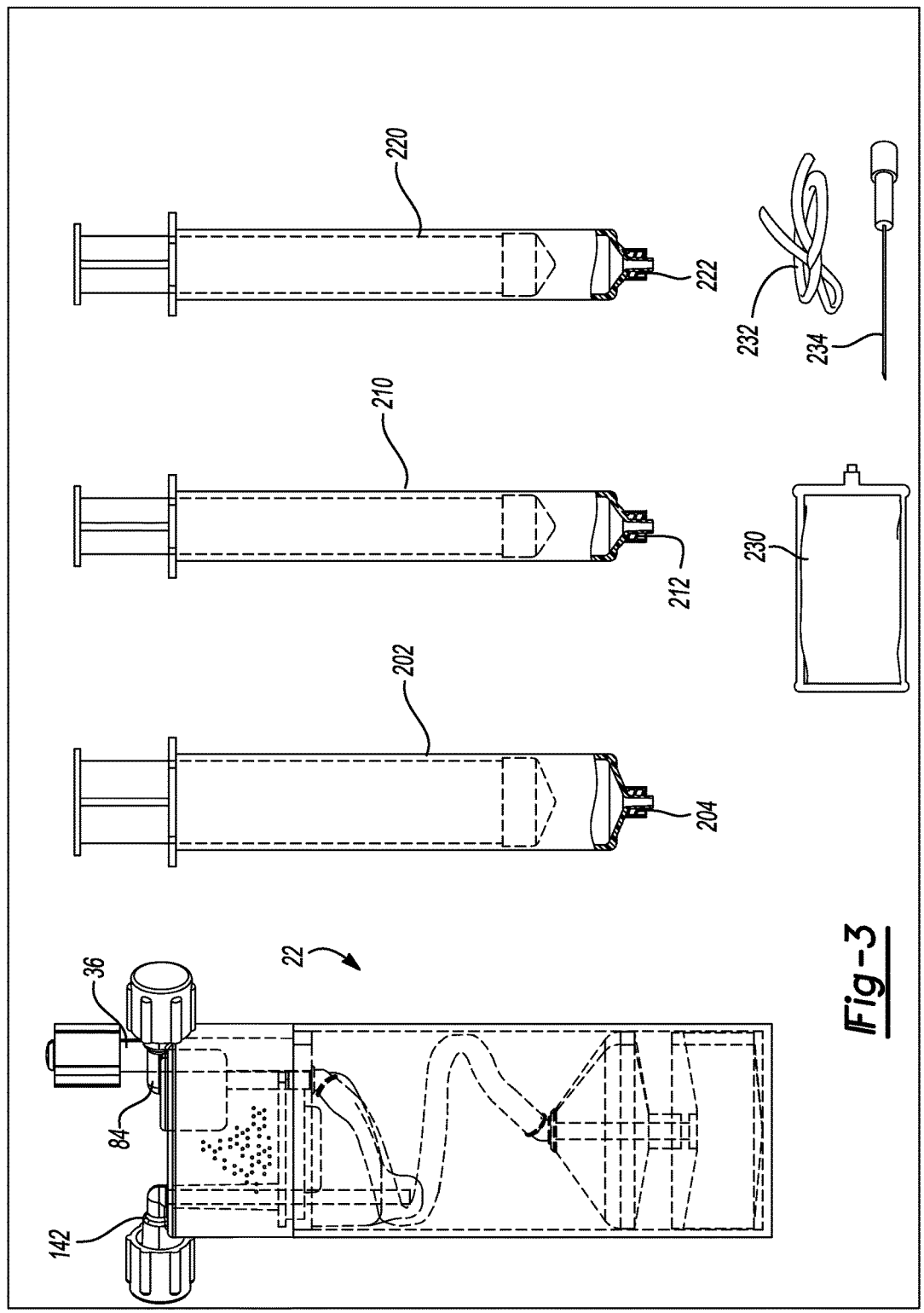

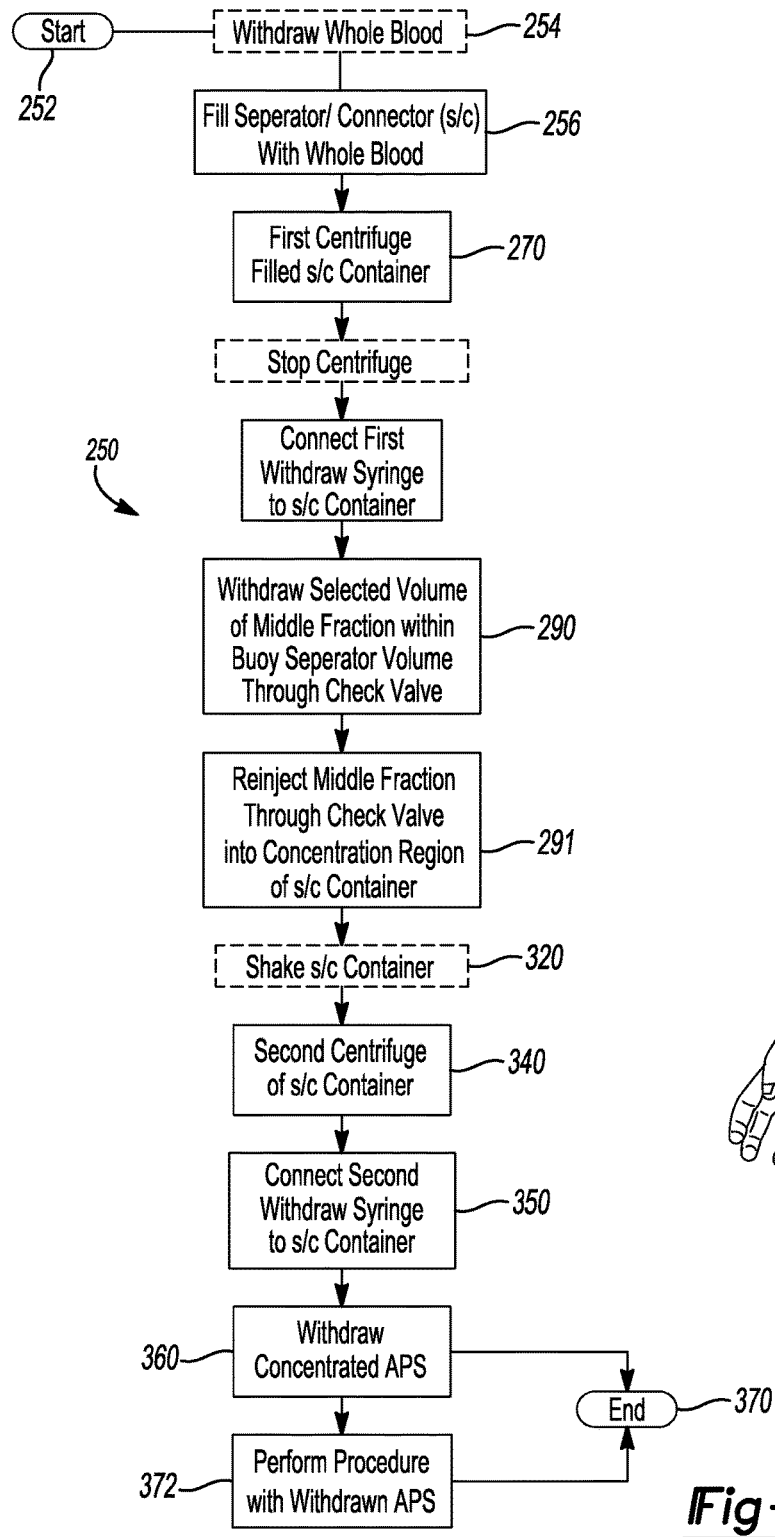
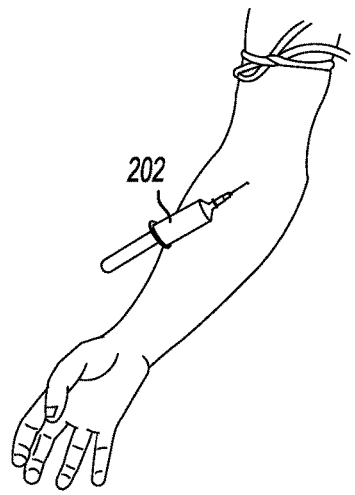
Fig-5A
Fig-4

US 9,808,568 B2

1

APPARATUS AND METHOD FOR SEPARATING AND CONCENTRATING A COMPONENT OF A FLUID

FIELD

The present disclosure relates to a method and apparatus for separating and concentrating a material; and particularly to separate a whole material into at least two fractions and concentrating at least one of the fractions in a single container.

BACKGROUND

This section provides background information related to the present disclosure which is not necessarily prior art.

Whole materials can be formed of multiple components that can form fractions. For example, whole blood, or other biological materials, can include various components that make up the whole. The various components of the whole material may be separated via gravity separation due to the varying densities of the components. Generally, centrifugation can be used to gravity separate different components of a whole material into fractions.

A centrifuge tube can be placed in a centrifuge after being filled with a selected whole material. The tube including the selected whole material can then be centrifuged at a selected speed and time for gravity separation of the whole material. The component of the whole material that is separated, however, remains at the original concentration of the selected. Accordingly, gravity separating does not generally concentrate any selected component.

A separation system can be provided that includes a container portion for concentrating a selected material generally by removing a selected material from a single container. Accordingly, to provide a concentrated material with a separation container is not generally known.

SUMMARY

This section provides a general summary of the disclosure, and is not a comprehensive disclosure of its full scope or all of its features.

A single tube separation and concentration system includes a separation volume and a concentration volume. Accordingly, a whole material can be positioned in a separation and concentration container to be a first separated in the separation volume and a selected fraction is moved to a concentration volume to be concentrated. The material can be moved to a collection sump from or within the concentration volume to allow for efficient removal of the concentrated material from the separation and concentration container.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a kit including at least the separating and concentrating container of FIG. 1;

FIG. 4 is a flow chart illustrating portions of a method for separating and concentrating a component;

FIGS. 5A-5E illustrate various portions of the method outlined in the flow chart of FIG. 4.

Corresponding reference numerals indicate corresponding parts throughout the several views of the drawings.

DETAILED DESCRIPTION

Example embodiments will now be described more fully with reference to the accompanying drawings.

Figure 1:
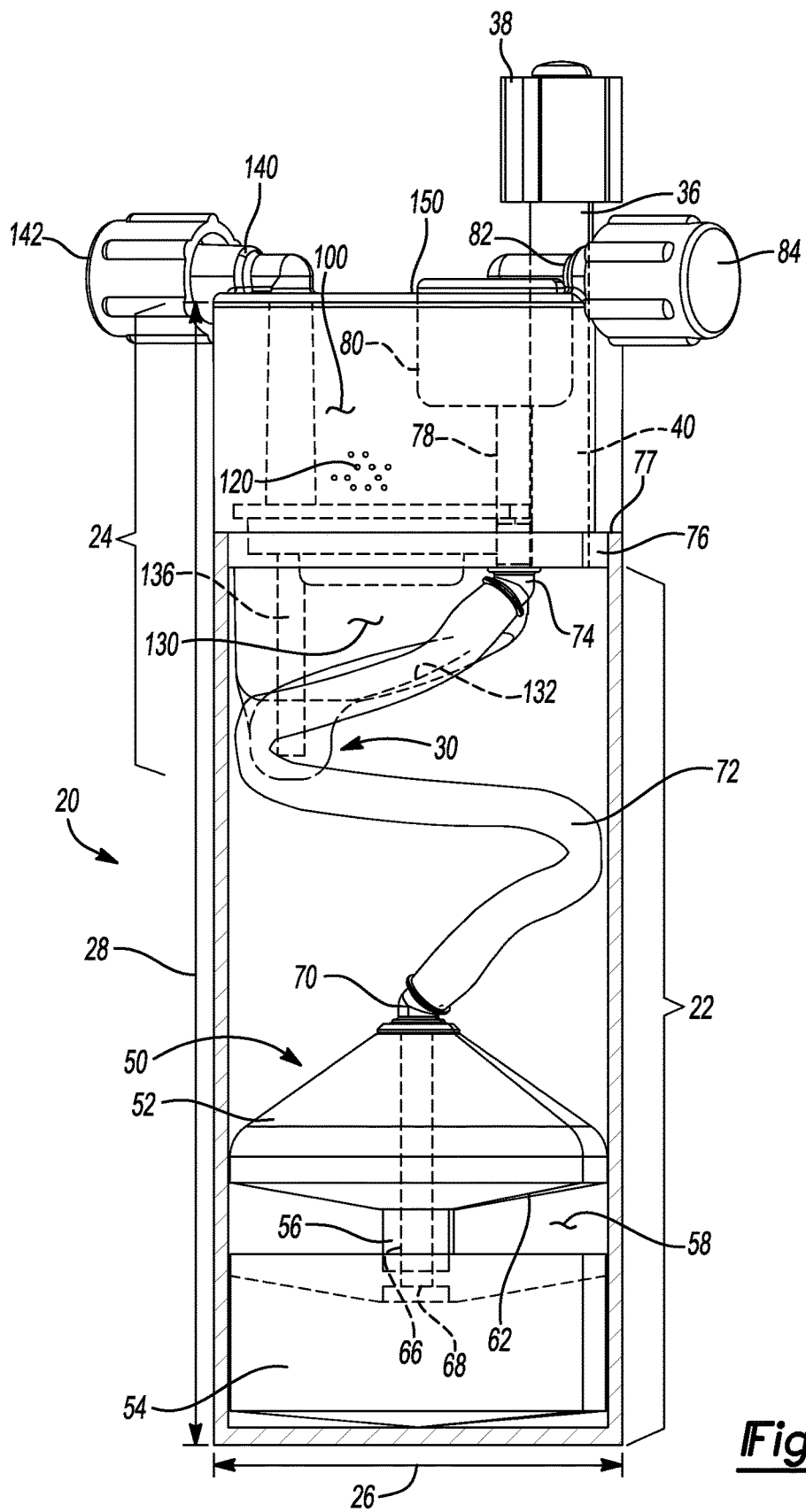
FIG. 1 is an elevation view of a separating and concentrating container.
Figure 2A:
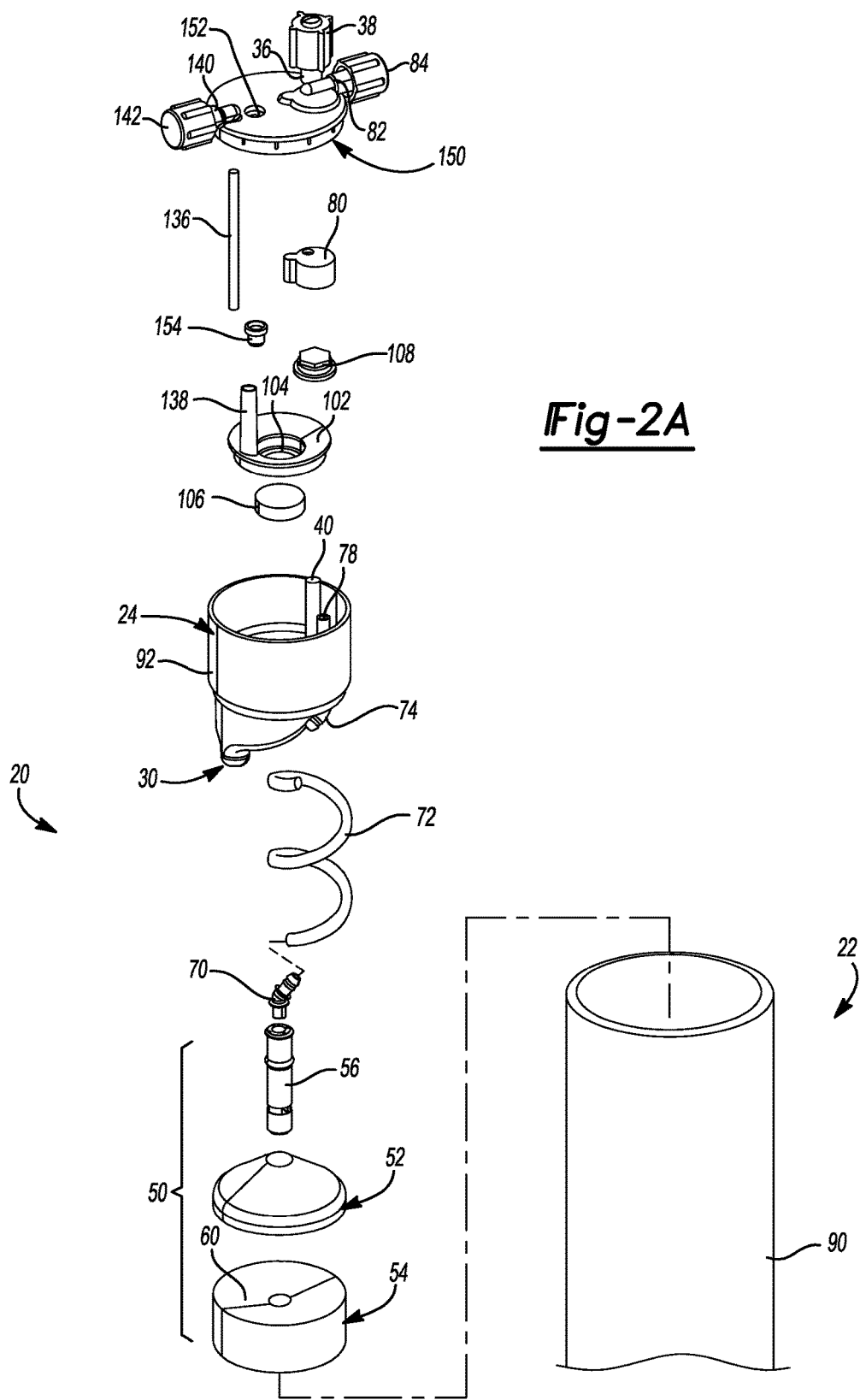
FIG. 2A is an exploded view of the separating and concentrating container of FIG. 1.
Figure 2B:
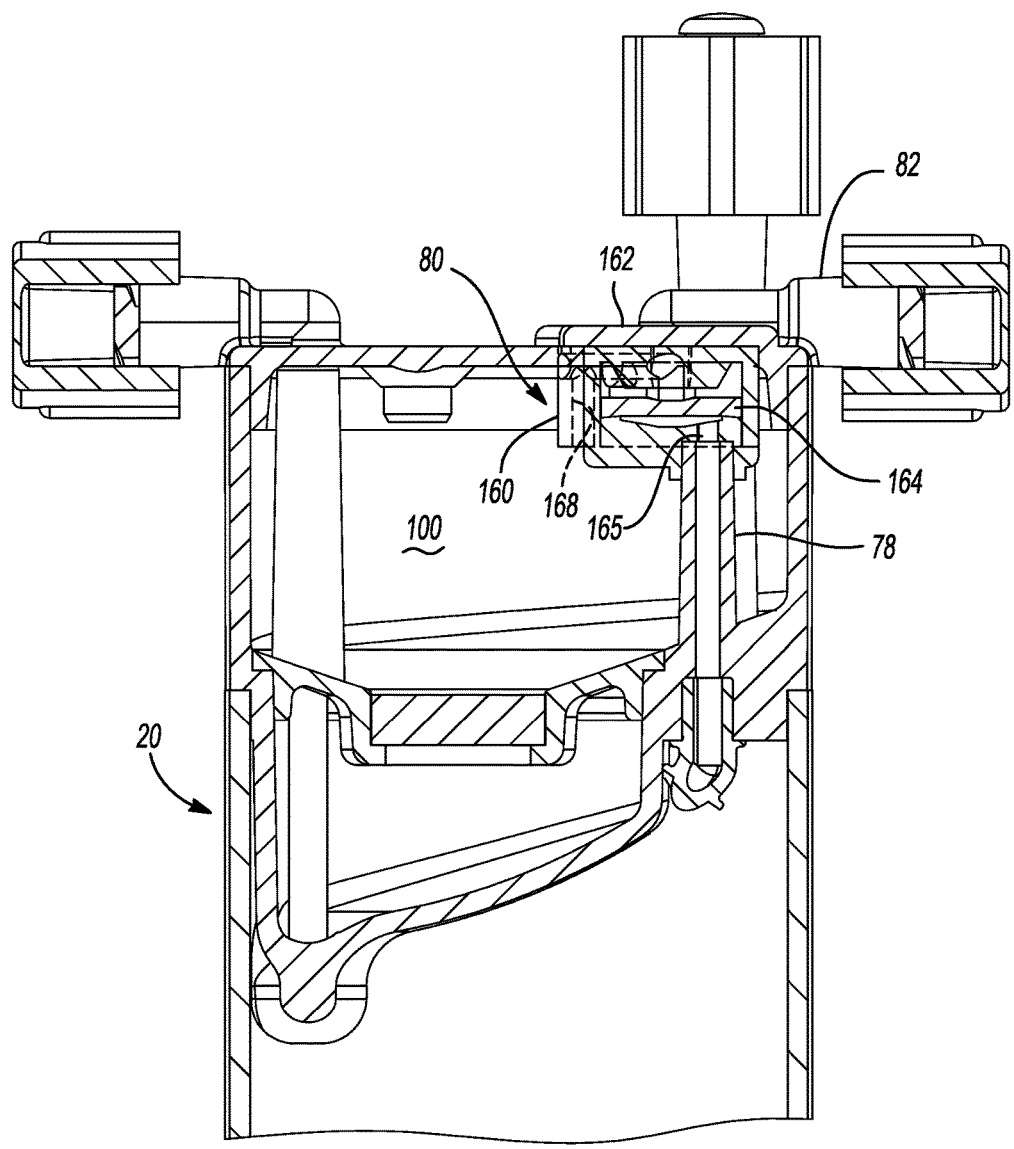
FIG. 2B is a detail cross-sectional view of a check valve assembly of the separating and concentrating container of FIG. 1.

With reference to FIGS. 1, 2A, and 2B, a separation and concentration container (S/C container) 20 is illustrated. The S/C container 20 generally includes a separation volume or region 22 and a concentration volume or region 24. The separation region 22 can contain a volume of whole material that can be first separated, via centrifugation, as discussed further herein. After centrifugation, a selected fraction of the separated whole material can be moved (e.g. drawn or expressed) into the concentration region 24 for concentration and removal from the S/C container 20. The S/C container 20 can generally include a selected dimension including a single or substantially uniform outer dimension, which can include an outer diameter 26 if the S/C container 20 is a cylinder. It is understood that the S/C container 20 need not be a cylinder, but a cylinder is exemplarily illustrated. The S/C container 20 can also include a height 28 that can include a dimension that is less than a combination of dimensions of the separation region 22 and the concentration region 24. As illustrated in FIG. 1, a portion of the concentration region 24, including a sump 30 and a sump wall 130, can extend from a portion of the concentration region 24 into an area of the separation region 22.

The separation region 22 can be initially filled through an inlet port 36 that can be selectively and/or temporarily capped with a cap 38. The inlet port 36 can include a selected type of port, such as a Luer Lok® port. Extending from the inlet port 36 can be an inlet tube 40 that passes through the concentration region 24 and allows material to be placed into the separation region 22 from the inlet port 36 to isolate the initial filling to only the separation section 22. Once material is positioned in the separation region 22, as discussed further herein, the S/C container 20 including the material (e.g. whole material) can be centrifuged or otherwise moved to apply a force to the S/C container 20 and any materials and devices placed therein.

The separation region 22 can also include and/or contain a buoy system 50 that can include a first buoy member 52, a second buoy member 54, and a third buoy member 56. Generally, the third buoy member 56 can be a connection member that connects the first buoy member 52 and the second buoy member 54. The buoy system 50 can include a selected buoy system, such as the buoy system generally used in the GPS® II or GPS® III gravity platelet separation system sold by Biomet, Inc. have a place of business in Warsaw, Ind. Buoy systems are disclosed in U.S. Pat. Nos. 7,845,499 7,806,276, and 7,992,725, all incorporated herein by reference.

The buoy system 50 can, however, include a selected density that can differ, if selected, from the buoy system generally included in the GPS® II system. For example, the buoy system 50 can include a density of about 1.05 grams per cubic centimeter (g/cm³) to about 1.08 g/cm³, including about 1.053 g/cm³ to about 1.083 g/cm³. Also, each of the members 52, 54, 56 of the buoy system 50 can have a different and selected density. For example, the first buoy member 52 can have a density of about 0.93 g/cm³ to about 0.955 g/cm³ and the second buoy member 54 can have a density of about 1.075 g/cm³ to about 1.095 g/cm³. The selected density of the buoy system 50 can be selected so that it is positioned within separated whole blood to allow for a selected separation of neutrophils, basophils, and monocytes in a region, also referred to as a buoy separation region or volume 58, between the first buoy member 52 and the second buoy member 54. The neutrophils, basophils, and monocytes may be included in the buffy coat, but may have a density slightly different than a complete portion or selected portions of the buffy coat. Accordingly, the density of the buoy system 50 can be selected to selectively position the buoy system 50, including the buoy separation volume 58 that is defined between the first buoy member 52 and the second buoy member 54.

As discussed further herein, the neutrophils, basophils, and monocytes can include a selected protein that can be useful in treating inflammation and pain. Selected inflammation can include arthritis or other joint inflammation diseases or injuries. Selected proteins can include, but are not limited to platelet growth factors (e.g. EGF, IGF-I, IGF-BI, PDGF-AB, PDGF-BB, VEGF), protein interleukin (e.g. IL-Ia, IL-4, IL-18, and Ir1L), and cytokines (e.g. sTNF-RI and sTNF-RII) that can be released and concentrated as further discussed herein to form an Autologous Protein Solution (APS).

The buoy system 50 can further include a selected geometry. For example, the second buoy member 54 can include a concave collection face 60 and the first buoy member 52 can include a convex collection face 62. According to various embodiments, the collection faces 60, 62 can be complementary in shape such that the two can mate so that substantially little area or volume is between the two collection faces 60, 62. According to various embodiments, the first buoy member 52 can move relative to the second buoy member 54 at various times. For example, as discussed further herein, when the volume within the buoy collection volume 58 is emptied, the first buoy member 52 can move relative to the second buoy member 54 to allow for change in volume when moving or removing a selected fraction from the collection volume 58. It will also be understood, as also discussed herein, that the first buoy member 52 can be fixe relative to the second buoy member 54 such that the buoy volume 58 is fixed.

The selected fraction can be removed from the collection volume 58 through the third buoy member 56 that can define a removal passage 66 that is connected with collection face passages 68. A connection elbow 70 can interconnect with the removal passage 66 to allow a vacuum to be formed through the connection elbow 70, the collection passage 66, and the buoy collection passages 68. A collection tube 72 can interconnect the connection elbow 70 with a withdrawal elbow 74 that extends from a wall 76 that can be a bottom wall of the concentration region 24. A second withdrawal tube 78 can be first connected with a check valve assembly 80 (discussed further herein) and a first withdrawal port 82 that can be selectively covered with a withdrawal cap 84. The first withdrawal port 82 can be connected with a withdrawal syringe with a Luer lock type connection or other appropriate connection. The withdrawal syringe can form a vacuum through the first withdrawal port 82, the check valve 80, the second withdrawal tube 78, the second elbow 74, the first tube 72, and the first connection elbow 70 and further through the buoy assembly as discussed above. Accordingly, the fraction of the whole material that is separated within the collection volume 58 defined by the buoy system 50 can be withdrawn to an exterior portion of the S/C container 20, such as within the first withdrawal syringe as discussed further herein.

The separation region 22 can generally be contained within a separation container member 90. The separation container member 90 can generally define the diameter 26, as discussed above. Additionally, the container 90 can allow for connection to or manufacturing with the concentration region 24. As illustrated in FIGS. 1 and 2A, the concentration region 24 can also generally be defined in a concentration container or member 92 that is fitted onto an end, (e.g. an open end), of the container 90. A shoulder 77 is defined near the wall 76 that allows the concentration container 92 to be fitted and/or seated in and on the container 90. The concentration region 24 can then be fixedly connected, such as via heat welding, friction welding, adhesives, or other materials to permanently fix the concentration region 24 to the container 90. Accordingly, the concentration container 92 can include an exterior wall and the sump portion 30 extending from the wall 76 of the concentration region. It will be understood, however, according to various embodiments, that the separation container 90 can be formed as a single member with the concentration region 24 using selected manufacturing techniques. Nevertheless, once the separation container 90 and the concentration container 92 are connected together they generally define the singe S/C container 20. Further, the S/C container 20 can generally define the single outer dimension 26 along the entire length 28 of the container 20.

Moreover, the concentration container 92 can be fitted at the end of the container 20 where the red blood cells concentrate. Thus, the concentration container 92 need note be fitted at a "top" or near where the lightest fraction would separate. This can also assist in moving the selected fraction 278, discussed herein, to the concentration section 22

As discussed further herein, once the selected fraction is withdrawn from the buoy separation volume 58 through the first outlet port 82, it can be re-injected into the concentration region 24, including an upper or initial volume 100, through the check valve assembly 80. In the initial volume 100 of the concentration region 24, an inner wall or seat portion 102 can have a central passage 104 in which a screen or filter 106 that can be held in place with a plug or holding portion 108. The selected or first fraction that is positioned within the initial or upper volume 100 of the concentration region 24 can be mixed with a plurality or volume of beads 120. The beads 120 can be a selected bead such as a bead formed of a polyacrylamide. The polyacrylamide material can interact with the neutrophils, basophils, and monocytes in the selected fraction to release the selected proteins which can include, but are not limited to platelet growth factors (e.g. EGF, IGF-I, IGF-BI, PDGF-AB, PDGF-BB, VEGF), protein interleukin (e.g. IL-Ia, IL-4, IL-18, and Ir1L), and cytokines (e.g. sTNF-RI and sTNF-RII), as discussed above. It will be understood that other selected materials can also be released and that the polyacrylamide can desiccate or remove water or moisture from the fraction withdrawn from the buoy separation region 58 and can also bind selected materials and proteins that are not selected for concentration within the concentration region 24. The beads 120 can interact with the selected fraction, as discussed further herein, including via shaking or centrifugation. The beads 120 are maintained within the initial concentration volume 100 by the filter 106.

After a selected time or at a selected time, the S/C container 20 can again be positioned in a centrifuge to force a separation of the concentrated material from the beads 120 by passing through the filter 106 to a second concentration volume 130 that is below or on an opposite side of the filter 106. The concentrated material can then collect within the sump 30 by travelling down an internal sump wall 132 and into the sump region 30. A third withdrawal tube 136 can extend into the sump 30 and pass through a nipple or passage 138 that extends from the internal wall 102 of the concentration region 24. The third withdrawal tube 136 interconnects with a second withdrawal port 140 that can be covered or capped with a cap 142. The second withdrawal port 140 can also be formed as a port like the inlet port 36 or the first withdrawal port 82 such as a Luer Lok® port. As discussed further herein, either the first withdrawal syringe or a second withdrawal syringe can be interconnected with the second withdrawal port 140 to withdraw the concentrated material from the sump 30 through the third withdrawal tube 36. The S/C container 20 can be dimensioned to operate with a selected centrifuge system such as the DRUCKER 755VES and/or the Thermo International Equipment Company IEC 7426, 7427, or 7428 centrifuge systems and the centrifuge system commonly used with the GPS® II gravitation platelet separation system sold by Biomet, Inc. having a place of business in Warsaw, Ind. Also, the S/C container 20 can include an outer dimension, shape, or portion that is keyed to an opening within the centrifuge such that the S/C container 20 will fit within the centrifuge in a specific and selected manner.

Each of the ports 140, 82, and 36 can extend through a top wall of the S/C container 20. The top wall can be a cap 150 that is dimension to fit within or interconnect with a top edge of the concentration region 24. It will be understood, however, that the top wall can also be integrally formed or formed as one piece of the concentration region 24 such as with the concentration container 92. Additionally, formed through or with the cap 150 can be a vent hole 152 that can include or be filled with a vent filter 154. The vent hole 152 can allow venting of the entire S/C container 20 during entry and removal of materials from the S/C container 20 to adjust for pressure and volume changes when introducing the whole material into the S/C container 20 and withdrawing at least portions of the whole material from the S/C container 20.

With continuing reference to FIGS. 1 and 2A and additional reference to FIG. 2B, the check valve assembly 80 will be discussed in further detail. As discussed above, the first outlet port 82 is interconnected with the check valve assembly 80. The check valve assembly 80 includes an external housing portion 160 that is fitted into the cap or upper wall 150. The check valve assembly 80 can further include a check valve cap 162 that can close or seal the check valve assembly 80. Within the check valve assembly 80 is a check valve member 164. The check valve member 164 can include a silicone disc or portion that is positioned within the check valve assembly 80. When a force acts upon the check valve disc 164, the disc 164 can flex upward or move upward towards the first outlet port 82 to allow flow of material into the check valve assembly 80 through the second outlet tube 78. When material is pushed back into the check valve assembly 80 from the first withdrawal port 82, such that material will enter the concentration region 24, the check valve disc 164 can flex down towards the second withdrawal tube 78 and close an opening 165 and thereby open a second opening 168 within the check valve assembly 80. The second opening 168 allows the fraction 278 to be pushed into the concentration region 24. Accordingly, the check valve assembly 80 including the check valve member 164 allows material to be drawn from the S/C container 20 and put back into the concentration region 24 for concentration of the selected fraction.

The S/C container 20 can be provided alone for use by a selected user and/or can be provided in a kit 200 as illustrated in FIG. 3. The kit 200 can include various other portions in addition to the S/C container 20. For example, the kit 200 can include an initial blood withdrawal syringe 202. The initial blood draw syringe 202 can include a Luer-Lok® syringe connection 204 (it is understood that the connection can be a Luer type connection or other appropriate connection as well) to interconnect with the inlet port 36. The blood draw syringe 202 can also be used to draw a blood sample directly from a patient or to provide a sample from a source, such as a blood bank site, a previously drawn sample, or other appropriate supplies of whole blood. The kit 200 can also include other processing syringes such as an initial withdraw syringe 210. The initial withdraw syringe 210 can also include a Luer Lok® connection 212 to interconnect with the first withdraw port 82. The first withdrawal syringe 210 can be used as discussed further herein, and briefly above, to withdraw the selected fraction from the S/C container 20 and reintroduce a selected portion of it into the concentration region 24. The kit 200 can further include a second withdrawal syringe 220 that can also include a Luer Lok® connection 222 to interconnect with the second outlet port 140.

It will be understood that the first and second withdrawal syringes 210, 220 need not be separate withdrawal syringes. Nevertheless, according to various embodiments, the separate withdrawal syringes can allow for a clean and sterile syringe to provide only the concentrated material for a selected procedure. That is the first withdrawal syringe 210 can include unconcentrated material that may not be completely clean or expressed back into the concentration region 24. Accordingly, the second withdrawal syringe 220 can be used to withdraw only the concentrated material from within the sump 30.

The kit 200 can further include other portions such as an anticoagulation agent 230, a tourniquet 232, a removable needle 234 (e.g. for connection with the blood withdrawing syringe 202) or other selected materials. It is understood, however, that the kit 200 can be provided with the S/C container 20 for ease of use and operation of the S/C container 20. The kit 200 can be used in a method for concentrating a selected component of a whole material, such as a selected component or fraction of whole blood. It will be understood, however, that the kit 200 need not be specifically used and that the S/C container 20 can be used in a separation and concentration procedure as discussed further herein, either alone or in combination with the other parts of the kit 200.

A method illustrated in the flow chart 250 in FIG. 4 can be used to separate and concentrate a selected fraction, such as the buffy coat or a portion of the buffy coat, from whole blood. Accordingly, the method 250 can begin in start block 252 and whole blood can be optionally withdrawn from a patient in block 254. According to various embodiments, whole blood can be withdrawn from a patient with the whole blood syringe 202 of the kit 200 as illustrated in FIG. 5A. Alternately, or in addition thereto, whole blood can be withdrawn with any appropriate syringe from any appropriate patient. Alternately, whole blood need not be drawn from a patient, as whole blood can be obtained from a supply, such as a blood bank or other whole blood or whole material supplies. Accordingly, withdrawing whole blood from a patient in block 254 is optional. Regardless, according to various embodiments whole blood can be withdrawn from a patient and the concentrated component can be reintroduced or applied to the same patient (i.e. autologous) in a selected procedure.

The S/C container 20 can be filled in block 256 with the appropriate supply of whole material. Accordingly, the whole blood withdrawn in block 254 can be supplied to fill the S/C container 20 or any other supply of whole material can be used to fill the S/C container 20 in block 256. It will be understood that the volume of the separation region 22 can defined a maximum volume that can be filled with an amount of whole material. According to various embodiments, the separation region can include a volume of about 50 milliliters to about 100 milliliters. It will be understood, however, that the volume of the separation region 22 can be selected for separating a selected amount of material. Nevertheless, according to various embodiments, about 55 to about 65, including about 60 milliliters of whole blood can be positioned in the separation region 22 when filling the S/C container 20 in block 256.

Figure 5B:
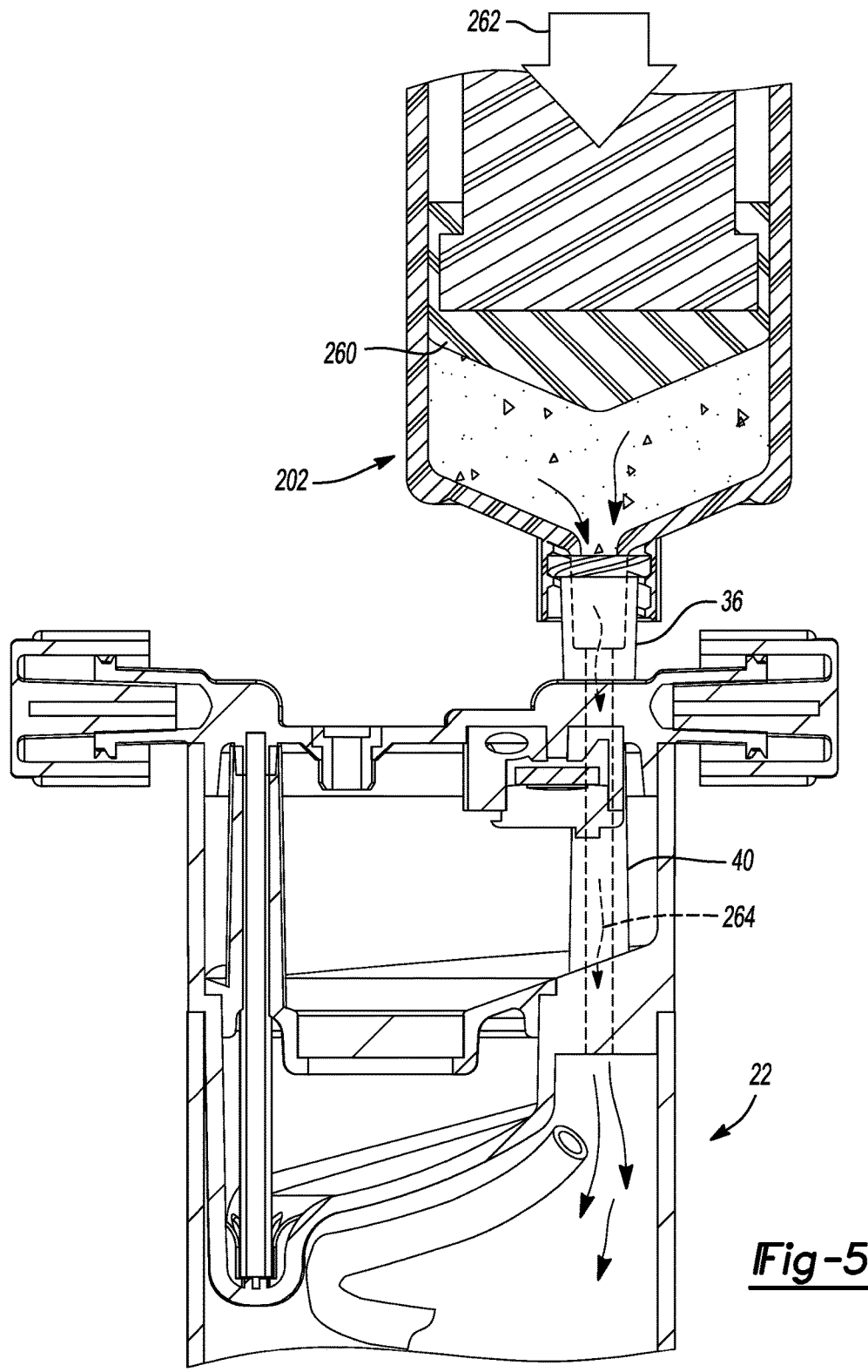

Filling the S/C container 20 in block 256 can include attaching the syringe 222 that can include a volume of whole material obtained from an appropriate source, such as a patient or blood supply, as illustrated in FIG. 5A, with the first inlet port 36 as illustrated in FIG. 5B. As discussed above, the inlet port 36 and the connection 204 of the syringe 202 can allow for a Luer connection between the inlet port 36 and the syringe 202. The connection can be made after removing the cap 38. As is generally understood, the syringe 202 can include a plunger 260 that is depressed or pushed generally in the direction of arrow 262 to inject the whole material through the inlet tube 40 generally in the direction of arrow 264 to fill or partially fill the separation region 22. The separation region 22 can be filled with an appropriate volume of whole material, including about 60 milliliters, as discussed above.

The whole material can be positioned within the separation region 22 prior to the application of a centrifugal force or increase gravitational force to cause separation of components of the whole material into fractions. It is understood that the whole material can include components that can be separated into fractions that are separated as layers within the container due to different densities and separation occurs after the application of a force. The whole material can enter the separation region 22 from the inlet tube 40 and generally spray or drip onto the buoy system 50 that is positioned within the separation region 22. It is understood that the separation region 22 can be provided to a user with the buoy system 50 having the various connections and tubes, including the first outlet tube 72, and connected to the concentration region 24 as illustrated in FIG. 1 and in the kit 200. The buoy system 50, if provided as a moveable buoy system where the first buoy member 52 can move relative to the second buoy member 54 can be substantially mated such that the first buoy member 52 is nested or close to the second buoy member 54. If the buoy system 50 is a fixed system, the buoy members 52, 54 can be fixedly separated as exemplarily illustrated in FIG. 1. Accordingly, a user need not assemble the S/C container 20 for use.

Once the S/C container 20 is filled in block 256, a first centrifuge of the S/C container 20 can occur in block 270. The S/C container 20 can be positioned in the centrifuge system appropriate for containing the S/C container 20. Accordingly, the centrifuge system can have openings or holders based upon the dimension of the S/C container 20. The S/C container 20 can include dimensions that are substantially similar to the GPS® II blood separation system container sold by Biomet. Accordingly, the centrifuge system can be similar to the centrifuge system used with the GPS® II blood separation system.

Figure 5C:
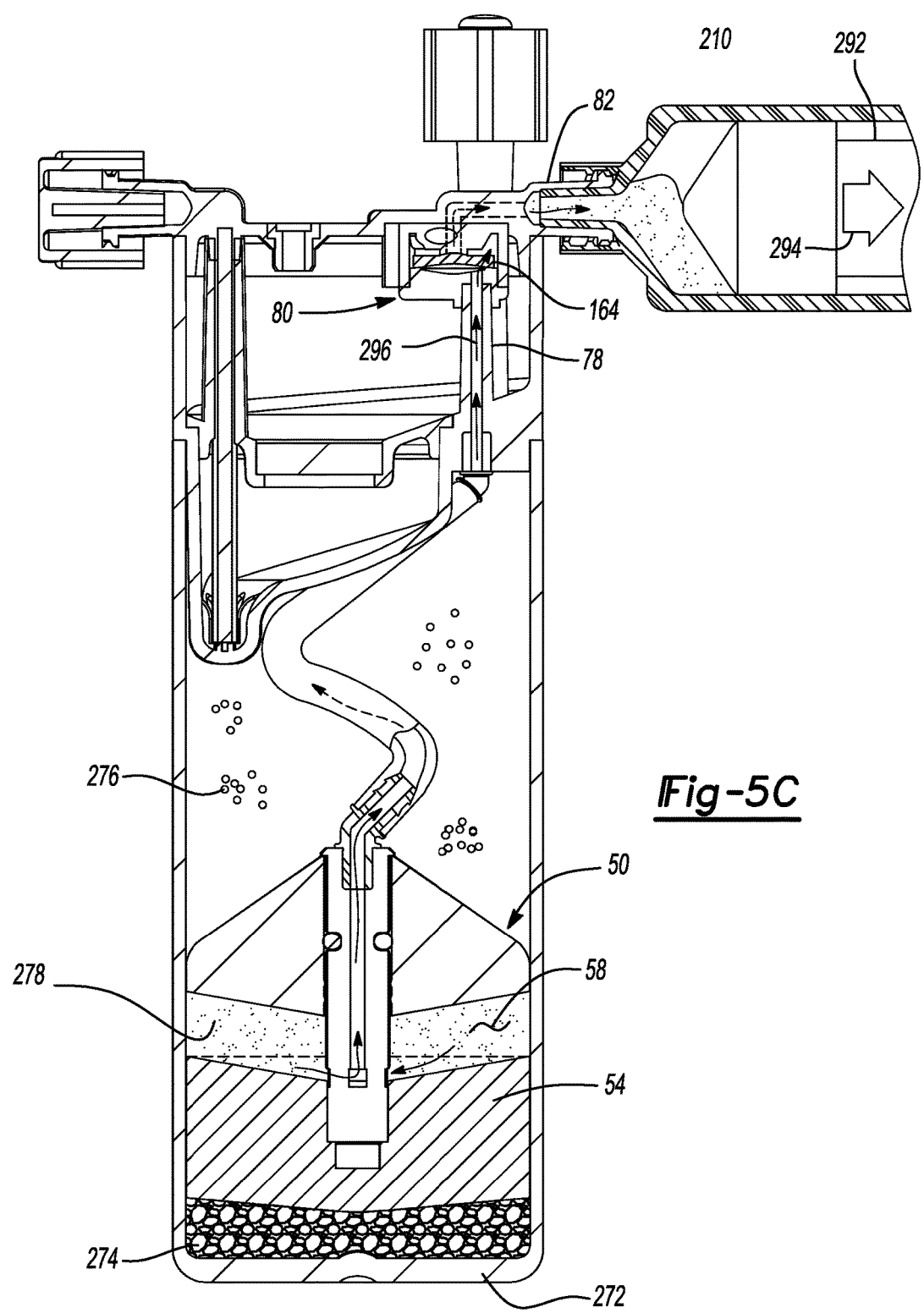

The first centrifugation of the S/C container 20 can be at about 3000 rotations per minute (rpms) to about 3500 rpms including about 3200 rpms for a selected time period. The selected time period of the first centrifugation in block 270 can be about 10 minutes to about 20 minutes, including about 15 minutes. The centrifuge speed and time can be selected to cause a substantial packing of red blood cells from a whole blood sample near a terminal end or bottom 272 of the S/C container 20 as illustrated in FIG. 5C. A red blood cell volume 274 can be positioned or separated to a volume or area between the second buoy member 54 and the terminal end 272 of the container 20. The red blood cells are generally the densest component of whole blood and therefore pack near the end or towards the direction of the centrifugal or increased gravitational force. Lighter or less dense components generally separate above the red blood cell volume 274. As illustrated in FIG. 5C, the buoy system 50 can also move upwards or away from the terminal end 272 and generally away from the direction of force of the increased gravity or centrifugation due to the selected density of the buoy system 50 being less than the red blood cell component of the whole blood sample.

Generally, a plasma fraction 276 will separate to an area between the first buoy member 52 and the cap or top 150 of the S/C container 20. Generally, the plasma is the least dense fraction of the whole blood sample and therefore will separate to an area furthest away from the terminal end 272 or the direction of the increased gravitational force. Accordingly, a middle fraction, which can include a buffy coat fraction 278, can separate to an area between the plasma fraction 276 and the red blood cell fraction 274 and generally within the buoy separation volume 58. As illustrated in FIG. 5C, the middle or buffy coat fraction 278 can be held within the buoy separation volume 58 after the selected centrifugation.

With continuing reference to FIG. 5C and FIG. 4, after the centrifugation in block 270, withdrawal of a selected volume of the middle fraction, which can also be referred to as the buffy coat, middle or selected fraction 278, can be withdrawn into a first withdrawal syringe in block 290. The first withdrawal syringe can include the syringe 210 of the kit 200 or can be any other appropriate syringe that can interconnect with the first outlet port 82. Again, the first outlet port 82 can include a Luer connection that can connect with the Luer fitting 212 of the first withdraw syringe 210. A plunger 292 can be moved in the direction of an arrow 294 to form a vacuum within the syringe 210 to draw the selected fraction 278 through the outlet port 82 generally in the direction of arrow 296. As discussed above, the third buoy member 56 can define the outlet passage 66 and the various connections and first and second outlet tubes 72, 78 can allow the fraction 278 to move from the buoy separation volume 58 generally in the direction of the arrows 296 and into the first withdraw syringe 210. Accordingly, the withdrawal syringe 210 can be operated to contain a portion or the entire fraction 278. Generally, the 60 milliliter whole blood sample will allow for the creation or separation of about 5 to 15 milliliters, including about 6 to 12 milliliters, and further including about 10 milliliters of the middle fraction 278.

Additionally, as discussed above, the fraction 278 can be withdrawn through the check valve assembly 80. The check valve assembly 80 that is connected to the outlet tube 78 to allow the fraction 278 to move into the syringe 210 to be withdrawn or removed from the S/C container 20. The check valve assembly 80, therefore, can allow the fraction 278 to be withdrawn to the syringe 210 until it is re-injected or reintroduced into the concentration region 24, as discussed above and further herein. This is allowed by the two way check valve assembly 80. Thus, the syringe 210 can remain connected directly to the S/C container 20 during the entire transfer of the fraction 278 from the buoy volume 58 to the concentration section 22. This can allow for efficient and ease of transfer of material. Additionally, this can reduce or eliminate cross-contamination, mislabeling or misplacement of the fraction 278.

Figure 5D:
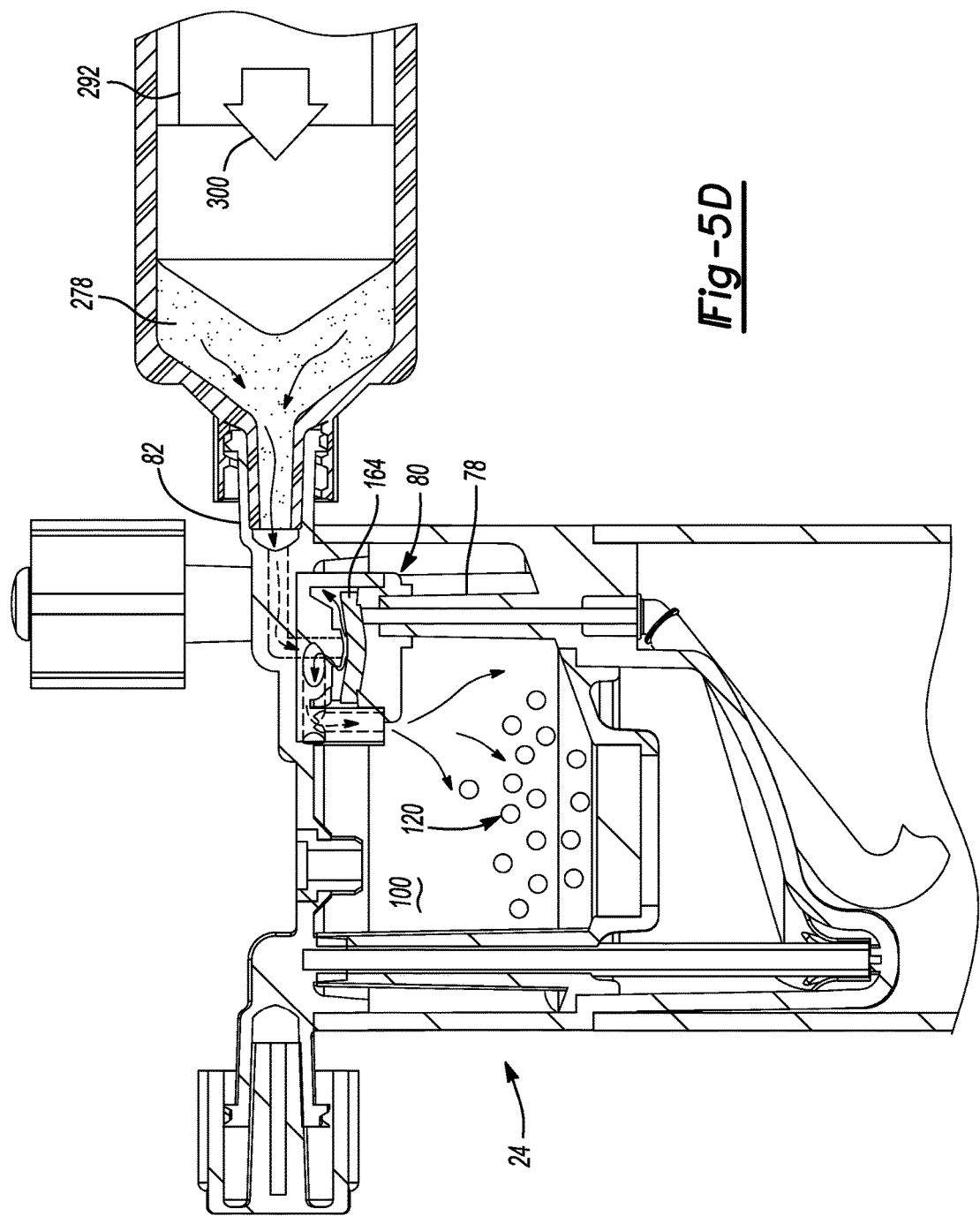

With continuing reference to FIG. 4 and additional reference to FIG. 5D, the first separation syringe 210, can remain connected or be reconnected to the first outlet port 82 and the plunger 292 can be moved in the direction of arrow 300 to re-inject the fraction 278 into the concentration region 24. The fraction 278 can be pushed through the check valve assembly 80 where the valve member 164 flexes or moves towards the second outlet tube 78 and allows the fraction 278 to move into the initial volume 100 of the concentration region 24 rather than back through the first outlet tube 78 and into the separation region 22. Accordingly, the middle fraction 278 can be re-injected into the S/C container 20 and specifically into the concentration region 24 in the blood 291. Once the fraction is moved into the first volume 100 of the concentration region 24, the S/C container 20, and particularly the concentration region 24 the selected fraction is mixed with the beads 120. The mixing can be optionally enhanced by initially shaking or agitating the S/C container 20 in block 320. The initial agitation can help mix the dehydrating or activating beads 120 with the fraction 278 that is injected into the initial volume 100 of the concentration region 24. It is understood, however, that the initial shaking in block 320 is not a requirement and that the beads 120 can simply be mixed by the injection of the fraction 278 or during a further centrifugation, as discussed herein. The beads 120 can include a polyacrylamide beads that can dehydrate the fraction 278, thus concentrating the fraction 278 to the concentrated fraction 278'. Also, the beads 120 can activate cells or portions of the fraction 278. As discussed above, the polyacrylamide beads can assist in releasing selected agents and proteins and concentrating the same for use in a procedure.

The initial shaking in block 320 can occur for appropriate time, such as about 30 seconds to about 90 seconds that further include about one minute. It will be understood, however, that the optional shaking can occur for appropriate time or be done as a part of a centrifugation step or be eliminated if selected.

Figure 5E:
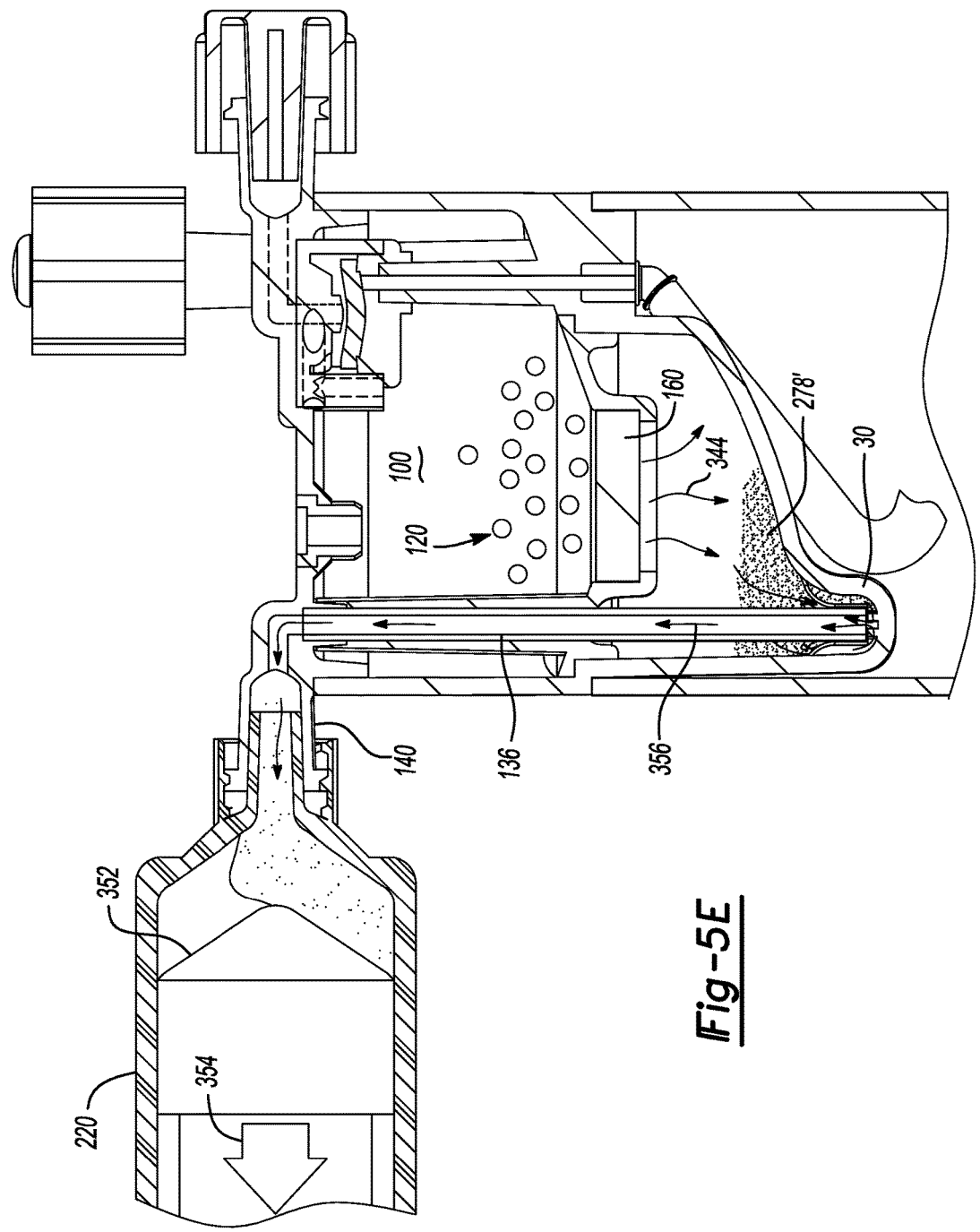

Regardless, after the initial optional shaking, if selected, the S/C container 20 can be replaced into the centrifuge device for a second centrifugation of the S/C container 20 in block 340. The second centrifugation in block 340 can be performed at a rotational speed of about 1500 rpms to about 4000 rpms, and including about 2000 rpms for a time period of about one minute to about five minutes and including about two minutes to about three minutes, and including three minutes. With reference to FIG. 5E, during the second centrifugation, the filter member 106 can hold the beads 120 in the initial volume 100 while the concentrated and/or activated materials can form a concentration fraction 278' that generally moves in the direction of arrow 344 down the wall 132 towards the sump 30. The concentrated fraction 278' can be formed based upon the interaction with the beads 120. The filter 160 can include a filter selected for separating an appropriate material or selected material from another portion of the fraction 278 or simply to hold the beads 120 within the initial volume 100. Regardless, the second centrifugation in block 340 allows the concentrated material to pass through the filter 160 and into the sump 30.

With continuing reference to FIG. 5E and FIG. 4, the second withdrawal syringe 220 can be connected to the second outlet port 140 to withdraw the concentrated fraction 278' in block 350. The second withdraw syringe 220 can include a plunger 352 that can be moved in the direction of arrow 354 to cause a vacuum within the syringe 220 to cause the concentrated fraction 278' to generally move in the direction of arrow 356 through the third outlet tube 136 and through the second outlet port 140. Again, it is understood, that the second withdrawal syringe 220 need not be a different withdrawal syringe, but can be the first withdrawal syringe 210 or can be provided separately from the kit 200. Regardless, the second withdrawal syringe can be connected in block 350 and the concentrated fraction 278' can be withdrawn in block 360.

The separation and concentration method 250 can end in block 370 if the material is to be withdrawn and used for a later procedure. Alternatively, or in addition thereto, the withdrawn and concentrated material can be used immediately in an intraoperative procedure in block 372. The intraoperative procedure can include an outpatient procedure where the volume of blood is withdrawn in a doctor's office, separated, concentrated as discussed in the method 250, and reintroduced for various treatments based upon medical or doctor's advice. Again, the separated and concentrated materials can include the selected proteins which can include, but are not limited to platelet growth factors (e.g. EGF, IGF-I, IGF-BI, PDGF-AB, PDGF-BB, VEGF), protein interleukin (e.g. IL-Ia, IL-4, IL-18, and Ir1L), and cytokines (e.g. sTNF-RI and sTNF-RII) to assist in treating inflammation and pain from various disease states. Additionally, the concentrated material can generally include about one to about five milliliters, further including about two to about three milliliters of the concentrated fraction 278' based upon an initial introduction of about 25 milliliters (ml) to about 100 ml, including about 60 milliliters whole blood into the S/C container 20. Accordingly, if additional concentrated amounts of the fraction volume 278' are selected, two of the S/C containers 20 can be filled simultaneously, such as to balance the centrifuge, to allow for the creation or separation and concentration of additional volumes. Nevertheless, the beads 120 can include about the one gram to about three grams, including about one gram of the polyacrylamide beads to interact with the fraction 278 that is positioned within the concentration region 24. It will be further understood that a different volume of beads can be selected based on a different volume of the fraction 278 introduced into the concentration region 24.

Accordingly, S/C container 20 can be provided in the kit 200 or separate from the kit 200 to separate and concentrate within the single container 20 a selected fraction of a whole material. As discussed above, a buffy coat or a portion of a buffy coat of a whole blood sample can be separated and concentrated in the S/C container 20. The S/C container 20 can include all portions and mechanisms to separate and concentrate the selected fraction of the whole blood sample with a centrifuge (or similar device) without requiring transport of a portion of the fraction to a separate container or operating region. Additionally, the S/C container 20 can allow for substantially efficient separation and concentration as user intervention is minimum and/or minimized save for introducing the whole sample and moving the fraction 278 to the concentration region 24. Additionally, user intervention is not required to determine the volume of the fraction 278 as the buoy system 50 defines the buoy separation volume 58 that contains the selected fraction 278 for later concentration. For example, the syringe 210, or similar container, can remain connected to the S/C container 20 during an entire duration of a movement of the fraction 278 from the buoy volume 58 to the concentration section 22. Also, the S/C container 20 can be maintained in a centrifuge during the movement as well.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What invention claimed is:

1. A method to separate and concentrate a component of a whole material, comprising:
    placing a whole material in a separation section of an integrated separation and concentration container;
    applying a first force to the integrated separation and concentration container to cause separation of the whole material such that at least a portion of the whole material moves towards a first terminal end of the integrated separation and concentration container;
    withdrawing the component from a buoy separation volume of a buoy system within the separation section;
    placing the withdrawn component into a concentration section of the integrated separation and concentration container;
    mixing the component in the concentration section with an activating/concentrating material; and
    applying a second force to the integrated separation and concentration container to remove at least a portion of the component from the mixture of the activating/concentrating material.

2. The method of claim 1, further comprising:
    withdrawing the removed portion of the component from the mixture of the activating/concentrating material from the a concentration section of the integrated separation and concentration container.

3. The method of claim 1, wherein the mixing the component in the concentration section with an activating/concentrating material causes a concentration of a selected portion of the component mixed with the activating/concentrating material such that the removed portion of the component is concentrated above a concentration of the selected component.

4. The method of claim 1, wherein mixing the component in the concentration section with the activating/concentrating material includes mixing the component with a polyacrylamide material.

5. The method of claim 1, wherein mixing the component in the concentration section with the activating/concentrating material includes releasing a selected protein from the component; and
    wherein applying the second force to the separation and concentration container to remove at least a portion of the component from the mixture of the activating/concentrating material includes moving the selected protein to a withdrawal portion of the concentration section.

6. The method of claim 2, further comprising:
    obtaining the volume of whole material from a patient; and
    applying the withdrawn removed at least a portion of the component to the patient.

7. The method of claim 1, wherein the first force is different than the second force.

8. The method of claim 1, further comprising:
    moving a plunger of a separation syringe in a first direction to apply the third force to the integrated separation and concentration container and draw the removed portion of the component into the syringe.

9. The method of claim 8, further comprising:
    moving the plunger in a second direction to apply a fourth force to the removed portion in the separation syringe to place the removed portion into the concentration section;
    wherein the first direction is opposite to the second direction.

10. The method of claim 9, wherein a check valve diverts the removed portion into the concentration section when the removed portion is forced from the separation syringe.

11. The method of claim 1, further comprising:
    agitating the integrated separation and concentration container when the withdrawn component is placed in the concentration section.

12. The method of claim 1, further comprising:
    filtering the removed portion of the component to prevent removing the activating/concentrating material from the concentration section.

13. The method of claim 12, further comprising:
    applying a fifth force to the integrated separation and concentration container to force the removed portion through a filter.

14. The method of claim 13, further comprising:
    collecting the filtered removed portion in a sump for removal from the integrated separation and concentration container.

15. The method of claim 1, further comprising:
    moving a plunger of a withdrawal syringe in a first direction to apply the second force to the integrated separation and concentration container to withdraw the removed portion.

* * * * *